United States Patent [19]

Burns et al.

[11] Patent Number: 6,095,980
[45] Date of Patent: Aug. 1, 2000

[54] PULSE INVERSION DOPPLER ULTRASONIC DIAGNOSTIC IMAGING

[75] Inventors: Peter N. Burns; David Hope-Simpson, both of Toronto, Canada

[73] Assignee: Sunnybrook Health Science Centre, North York, Canada

[21] Appl. No.: 09/156,097

[22] Filed: Sep. 17, 1998

Related U.S. Application Data

[60] Provisional application No. 60/060,846, Oct. 2, 1997.

[51] Int. Cl.[7] ........................................................ A61B 8/00
[52] U.S. Cl. ............................................ 600/453; 600/458
[58] Field of Search .................................. 600/443, 447, 600/453, 458, 454–456

[56] References Cited

U.S. PATENT DOCUMENTS

| | | | |
|---|---|---|---|
| 4,610,255 | 9/1986 | Shimura et al. | 600/443 |
| 5,410,516 | 4/1995 | Uhlendorf et al. . | |
| 5,577,505 | 11/1996 | Brock-Fisher et al. . | |
| 5,628,322 | 5/1997 | Mine . | |
| 5,632,277 | 5/1997 | Chapman et al. | 600/443 |
| 5,706,819 | 1/1998 | Hwang et al. . | |

FOREIGN PATENT DOCUMENTS

WO 98/20361   5/1998   WIPO .

OTHER PUBLICATIONS

T. Christopher, Finite Amplitude Distortion–Based Inhomogeneous Pulse Echo Ultrasonic Imaging, IEEE Trans. Ultr., Ferroelec. & Freq. Control, vol. 44, No. 1, Jan. 1997 at pp. 125.

P.N.Burns et al., Harmonic Power Mode Doppler Using Microbubble Contrast Agents, J.E.M.U. V. 16, No. 4 at pp 132–42 (Masson, Paris, 1995).

P.N. Burns, Harmonic Imaging with Ultrasound Contrast Agents, Clin. Radiol. vol. 51, supp. 1 at pp 50–55 (Great Britain 1996).

P. N. Burns et al., Harmonic Imaging Principles and Preliminary Results, Angiology, vol. 47, No. 7 Part 2 at pp S63–S74 (New York Jul. 1996).

P.N. Burns, Presentation of Papers Nos. 241, 243, 1046, 1438, 1682, 166 and 169, Supplements to Radiology (Nov. 1992 v. 185; Nov. 1993 v. 189; Nov. 1994 vol. 193; Nov. 1995 v. 197; Nov. 1996 v. 201).

*Primary Examiner*—Francis J. Jaworski

[57] ABSTRACT

An ultrasonic diagnostic imaging method and apparatus are presented which separates broadband linear and nonlinear echo signal components while simultaneously distinguishing the effects of motion. The inventive method maps ultrasonic echo signals in the r.f. (time) domain to Doppler shift frequencies in the Doppler domain in a way that depends upon the linearity of the echoes. The inventive method does this by analyzing the phase shifts between successive echoes. Apparatus is described in which a Doppler echo ensemble is acquired by a transmit sequence of cyclically phase-varying waveforms. When the echoes of the ensemble are combined during Doppler processing, the resulting Doppler spectrum is divided into separate regions, with odd harmonics (e.g., linear signal components) residing in one region and even harmonics (e.g., second harmonic signal components) residing in another region. In a preferred embodiment a Doppler wall filter is used to delineate a particular type of signal information for processing, such as tissue motion, harmonic contrast agent, or tissue harmonic imaging information.

76 Claims, 7 Drawing Sheets

PULSE INVERSION DOPPLER ULTRASONIC DIAGNOSTIC IMAGING

This application claims the benefit of U.S. Provisional Application Ser. No. 60/060,846 filed Oct. 2, 1997.

This invention relates to methods and apparatus for performing ultrasonic diagnostic imaging and, in particular, to the detection and processing of echoes from linear and nonlinear ultrasonic scatterers by a new technique of pulse inversion Doppler.

In recent years two new diagnostic ultrasound imaging techniques have emerged which make use of nonlinear signals instead of the conventional linear signals. In conventional ultrasonic imaging the echoes which are reflections of the transmitted waveform are received, detected and used to form an image. These echoes are referred to as linear echoes because they mirror the transmitted waveforms in virtually all respects, including frequency and waveshape, differing only due to amplitude attenuation caused by absorption of acoustic energy. The amplitude-reduced correspondence of the echoes means that the echoes are linearly related to the transmitted waveform, hence the term linear imaging.

Received echoes can also contain nonlinear signal components from several sources. These components bear a nonlinear relationship to the transmitted waveform. One source of nonlinear effects is the distortion that the transmitted waveform undergoes as it passes through tissue. As the acoustic wave travels through tissue the velocity of the compressional phase of the wave will exceed the velocity of the rarefactional phase. The differing velocities of the two phases of the transmitted wave cause progressive distortion of the waveform as it travels through tissue, giving rise to harmonic components of the original wave frequency. When these distorted waveforms are reflected, the returning echoes will contain these distortions and the received echoes will contain energy at the fundamental frequency and at higher harmonics of the fundamental. The detection and imaging of these naturally occurring harmonics of the transmitted waveform is referred to as tissue harmonic imaging.

A second source of nonlinear echo components is microbubble contrast agents. Today's new generation of contrast agent will, when insonified at a sufficient energy level, resonate in an irregular, nonlinear manner, thus becoming responsive sources of nonlinear acoustic energy. This nonlinear energy, as well as fundamental frequency energy, is propagated back to the transducer where it can be received, processed and displayed. When even higher energy levels are transmitted to the microbubbles the microbubbles are disrupted by the transmitted sound, producing strong echoes which change significantly from pulse to pulse and can be readily detected and displayed. In either case these strong nonlinear microbubble responses can be used to produce highly distinct images of the fluid containing the microbubbles.

The conventional method of separating linear and nonlinear signals is on the basis of frequency using filters. A received echo containing fundamental and harmonic signals can be lowpass or bandpass filtered to pass the fundamental frequency signals and block the second harmonic signals. The signal can be highpass or bandpass filtered at a higher band of frequencies to pass the second harmonic signals to the exclusion of the fundamental frequencies. Filter separation of fundamental and harmonic energy is band-limited by the passband of the bandpass filter used, and is not completely effective when there is a frequency overlap of fundamental and harmonic energy.

A greatly improved technique for separating fundamental and harmonic signals which obviates the need for filters and their limitations is described in U.S. Pat. No. 5,706,819. This patent, of which one of us is a co-inventor, describes a technique called "pulse inversion" which separates fundamental and harmonic signal components by signal processing. In the pulse inversion technique, two oppositely phased waveforms are transmitted and echoes received after each transmission. The two echo sequences are then summed or subtracted on a spatial basis. When the echoes received from a location are summed, the linear components, being linearly related to transmit waveforms and differing only in phase, will cancel by reason of their phase opposition. A significant portion of the nonlinear echo components from successive pulses will not be in phase opposition but will additively combine. Correspondingly, when two echoes from a location are subtracted the oppositely phased fundamental (or linear) components will reinforce each other while a significant portion of the nonlinear components are canceled by subtraction.

Since pulse inversion separation does not rely upon filters, it is effective for separating broadband signals, even when fundamental and harmonic components are somewhat overlapping in frequency. However, since pulse inversion is a two-pulse method, it is subject to motion artifacts. In particular, the pulse inversion method cannot distinguish motion from nonlinear echoes, since a response will be produced in either case. Accordingly, it would be desirable to be able to detect and separate the Doppler shifts of linear and nonlinear components of the echo. It would further be desirable to fully separate not just linear and nonlinear signal components, but also to be able to distinguish nonlinear echo components from motional effects. It would also be desirable for such signal separation to be broadband in operation and not inhibited by the constraints of an r.f. (radio frequency) filter circuit.

In accordance with the principles of the present invention, an ultrasonic diagnostic imaging method and apparatus are presented which separates broadband linear and nonlinear echo signal components while simultaneously distinguishing the effects of motion. The inventive method maps ultrasonic echo signals in the r.f. (time) domain to Doppler shift frequencies in the Doppler domain in a way that depends upon the linearity of the echoes. The inventive method does this by analyzing the phase shifts between successive echoes received in response to a modulated transmission sequence. In accordance with our inventive method, a Doppler echo ensemble is acquired by a transmit sequence of cyclically phase-varying waveforms. When the echoes of the ensemble are combined during Doppler processing, the resulting Doppler spectrum is divided into separate regions, with odd harmonics (e.g., linear signal components) residing in one region and even harmonics (e.g., second harmonic signal components) residing in the other region. Each region spans a range of frequencies corresponding to the motion of the materials being imaged, including the absence of motion in linear and nonlinear echoes from stationary materials in the body. In a preferred embodiment a Doppler filter is used to simultaneously delineate a particular type of signal information for processing, such as tissue motion, harmonic contrast agent, or tissue harmonic imaging information. Apparatus for carrying out the inventive method is also described.

Figure 1:
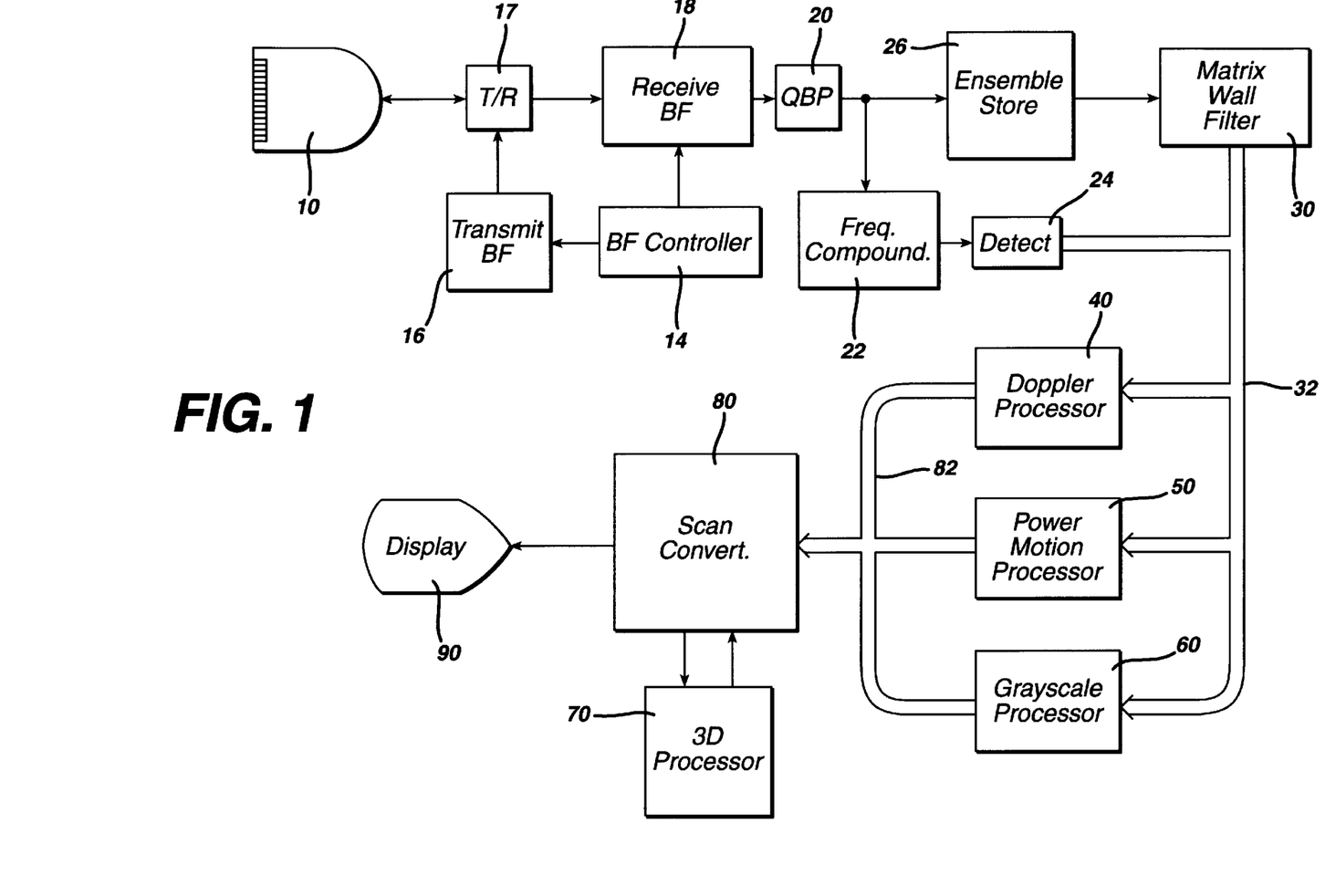
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A probe 10 which includes an array transducer 12 transmits ultrasonic energy into the body and receives echoes returned from tissue, cells and flowing substances in the body, including ultrasonic contrast agents when used. The array transducer can be a linear or curved array, and can be operated as a phased array or linear array. Phased array operation is often preferred for Doppler studies. The timing of transmission and reception by the array transducer is synchronized by a beamformer controller 14 which is connected to a transmit beamformer 16 and a receive beamformer 18. The channels of each beamformer are connected to the individual elements of the array transducer so as to separately control the transmission and reception of signals from the individual elements. The transmit beamformer 16, under control of the beamformer controller, determines the time at which each element in the array is actuated to transmit a wave or pulse. This controlled timing of transmission enables the wave transmitted by the entire array to be steered in a given direction, that is, along a predetermined scanline, and to be focused at the desired depth of focus. The channels of the two beamformers are coupled to elements of the array by transmit/receive switches 17 which protect the receive beamformer channel inputs from high transmit voltages.

The echoes received by individual transducer elements are coupled to individual channels of the receive beamformer 18 by the transmit/receive switches 17. These input paths may also include preamplifiers to amplify the received echo signals and time gain compensation circuits to offset the effects of depth dependent attenuation. When the receive beamformer 18 is a digital beamformer as it is in the preferred embodiment, each channel of the beamformer is preceded by or includes an analog to digital converter. The channels of the beamformer continuously appropriately delay the echoes received by each transducer element from along the scanline so that the signals received from common points (sample volumes) along the scanline are brought into time coincidence. The continual delay variation effects dynamic focusing of the received echo signals along the scanline. The signals at the outputs of the channels are then combined to form a sequence of coherent echo signals.

Receive beamformers also conventionally perform other processing operations such as normalization of signal amplitudes to offset the effects of dynamic aperture changes. The receive beamformer may also be partitioned into two or more groups of channels, each with its own unique delay programming from the beamformer controller, to perform multiline reception. In multiline reception, each group of channels steers and focuses a received beam along its own scanline, thereby forming two or more received scanlines simultaneously. While multiline reception can increase frame rate by acquiring all of the scanlines of one image in less time, it is prone to aberration effects, since not all of the received scanlines are coincident with the transmit aperture.

The sequence of coherent echoes received along the scanline can now be detected, scaled to a range of grayscale values, scanconverted to the desired image format, and displayed, thus forming a B mode image. In the apparatus of FIG. 1, the coherent echoes are demodulated by a quadrature bandpass (QBP) filter 20 into inphase (I) and quadrature (Q) samples. The I,Q samples can be Doppler processed to determine Doppler power, velocity, acceleration, variance, and the direction of flow or motion, and can also be used to detect the amplitude of the echo signal by the algorithm $(I^2+Q^2)^{1/2}$. For B mode imaging in the embodiment of FIG. 1, the I,Q samples are processed to remove speckle by frequency compounding circuit 22. The echo amplitude is detected by a detector 24 and the detected echo signals are applied to a grayscale processor 60 by way of an echo data bus 32, where the echoes undergo log compression and are grayscale mapped. Details of a preferred technique for log compression and grayscale processing are found in U.S. Pat. No. 5,993,392. The grayscale signals are coupled to a scan converter 80 by way of an image data bus 82, where the R-θ scanline data is converted to the desired display format. The scan converted image is displayed on a display 90.

A detailed description of the QBP filter 20, the frequency compounding circuit 22, and the detector 24 may be found in U.S. Pat. [appl. Ser. No. 08/893,426].

For Doppler imaging the scanline is repetitively scanned over an interval of time to gather a sequence of temporal echoes at each sample volume along the scanline. This temporal echo sequence, called an ensemble, is acquired by a sequence of transmit waves, the repetition frequency of which is called the pulse repetition frequency, or PRF. Each individually transmitted wave or pulse exhibits a nominal frequency called the Doppler frequency which is in the normal r.f. range of diagnostic ultrasound. PRFs are usually in the kiloHertz range or lower. The echo ensembles are accumulated in an ensemble store 26 from which completed ensembles are produced for Doppler processing.

The conventional first step in Doppler processing is wall filtering. When imaging or measuring bloodflow in the heart and blood vessels, the relatively low level echoes from blood cells can be overwhelmed by strong echoes reflected by nearby tissue such as a vessel or heart wall. Since the intent of the procedure is to image or measure bloodflow, the tissue echoes are, in this instance, clutter which can be eliminated. The circuitry which eliminates these unwanted signals is called a wall filter, since its basic purpose is to eliminate echoes from the heart and vessel walls. These signals may be discriminated by amplitude, frequency, or a combination of these two characteristics since tissue signals are generally of greater amplitude and lower frequency than bloodflow signals. A preferred technique for eliminating tissue signals as well as Doppler artifacts known as "flash" is shown in U.S. Pat. No. 5,197,477.

The wall filter may also be operated with a reverse characteristic so as to pass tissue Doppler signals to the exclusion of bloodflow Doppler signals. When these signals of the tissue are Doppler processed, images of moving tissue such as the heart muscle and valves can be produced. This imaging technique is known as tissue Doppler imaging.

The filtered Doppler signals, bloodflow or tissue, are applied to a Doppler processor 40 where they are used to perform Doppler estimation of the Doppler phase shift or signal intensity (power Doppler). Conventionally this is done by Fourier transform or autocorrelation of the Doppler signal data. A preferred technique is to perform a two dimensional autocorrelation which simultaneously estimates the Doppler phase shift and the reference or center frequency of the Doppler signal. The latter is useful for correction of the effects of depth dependent frequency attenuation in the phase shift estimation. Such a two dimensional Doppler processor is described in U.S. Pat. No. 5,386,830. Since the Doppler frequency or phase shift is proportional to the velocity of the bloodflow or tissue which returned the echoes, the production of a velocity, acceleration or variance number is straightforward. In colorflow Doppler the velocities of bloodflow are mapped to a color scale, coupled to the scan converter 80 over the image data bus 82, and overlaid on a grayscale image of the tissue structure containing the bloodflow. In power Doppler imaging the intensity of the Doppler signals is similarly mapped and displayed on a grayscale image. Doppler and grayscale image data can also be processed by 3D processor 70 to form three dimensional image presentations of the bloodflow and/or tissue, as described in U.S. Pat. Nos. 5,474,073 and 5,720,291.

Figure 2:
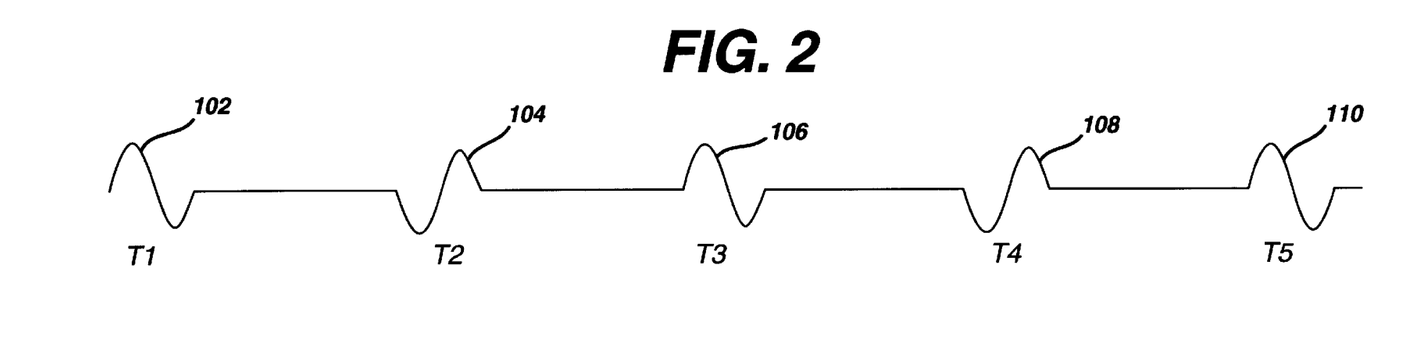
FIG. 2 illustrates a preferred transmit waveform sequence for acquiring an echo ensemble in accordance with the principles of the present invention.

In accordance with the principles of the present invention, the echo ensemble is acquired by a sequence of transmit waves exhibiting a different phase from wave to wave. In a preferred embodiment the phase alternates by 180° from wave to wave as shown by the pulse sequence of FIG. 2. For ease of illustration these pulses are shown as single cycles of a sine waveform, although longer pulse cycles or unipolar pulses may also be employed depending upon the intent of the imaging procedure. In the drawing pulse 102 is transmitted at time T1, after which a sequence of echoes from along the scanline are acquired, the first sample in each ensemble. At time T2, which is separated from time T1 by an interval called the pulse rate interval (PRI), pulse 104 is transmitted which is seen to be the inverse of pulse 102; pulse 104 is 180° out of phase with pulse 102. In similar manner the phases of pulses 106, 108, and 110 at times T3, T4, and T5 are alternated by 180° from pulse to pulse.

Figure 3:
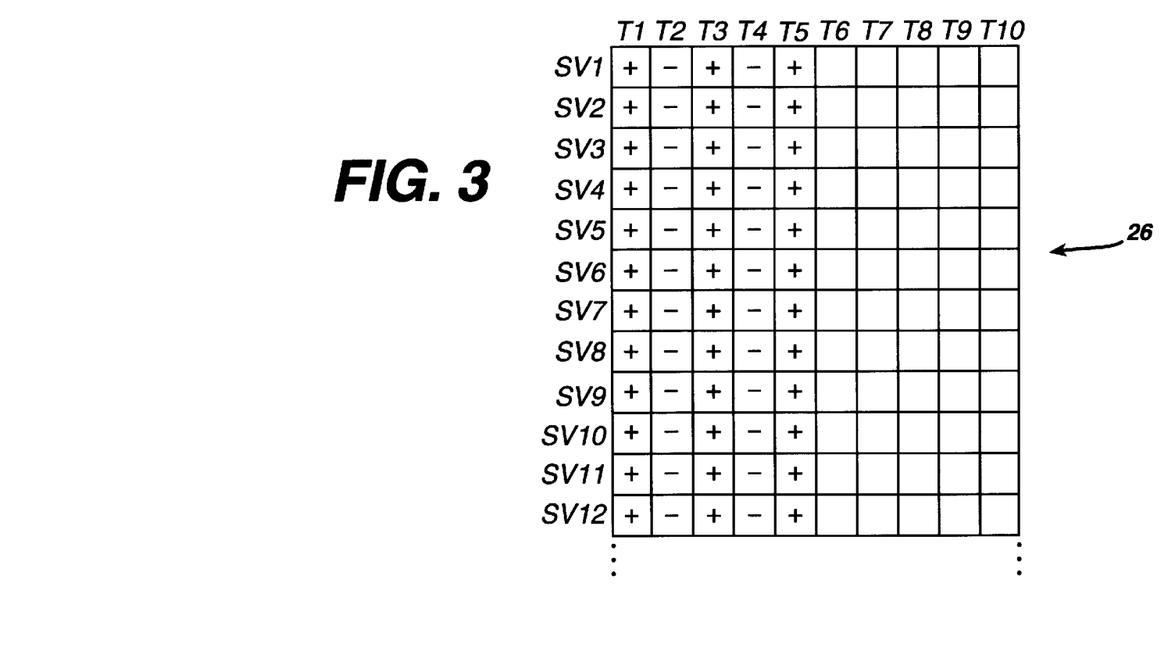
FIG. 3 diagrammatically illustrates the ensemble store of FIG. 1.

As echoes are received following each pulse another sample is added to each ensemble as shown in FIG. 3, which illustrates the purpose of the ensemble store 26. The echoes received from consecutive sample volumes (SV#) along the scanline in response to transmit pulse 102 are stored in the first column of the ensemble store, as indicated by the "+" symbols in the column headed T1. The echoes received from sample volumes along the scanline in response to transmit pulse 104 are stored in the second column of the ensemble store, as indicated by the "−" symbols in the column headed T2. The rest of the columns T3–T5 are filled in by echoes received in response to pulses 106, 108, and 110.

The ensemble of each sample volume SV then undergoes wall filtering in wall filter 30. In a preferred embodiment the wall filter is a matrix filter. Matrix wall filtering is performed by selection of appropriate multiplier coefficients and the matrix filtering is of the form $$\begin{bmatrix} y_1 \\ y_2 \\ y_3 \\ \vdots \\ y_n \end{bmatrix} \begin{bmatrix} a_{11} a_{12} a_{12} & \cdots & a_{1n} \\ b_{11} b_{12} b_{12} & \cdots & b_{1n} \\ c_{11} c_{12} c_{12} & \cdots & c_{1n} \\ \vdots & & \vdots & \vdots \\ n_{11} n_{12} n_{12} & \cdots & n_{1n} \end{bmatrix} \cdot \begin{bmatrix} x_1 \\ x_2 \\ x_3 \\ \vdots \\ x_n \end{bmatrix}$$

where $x_1 \ldots x_n$ are samples of an ensemble and $Y_1 \ldots y_n$ are filtered output values. The $y_n$ products of the echo values and coefficients are echo values filtered in accordance with the characteristic determined by the coefficients. The coefficients are chosen in consideration of the filter characteristic desired, in particular, with regard to the desired filter impulse response.

In accordance with a further aspect of the present invention, the combinatorial processing of the matrix wall filter effects a separation of linear and nonlinear components of the echo signals. As will be discussed below, this separation arises by virtue of the phase shift introduced into the Doppler values by the phase alteration of the transmit signals.

Figure 4A:
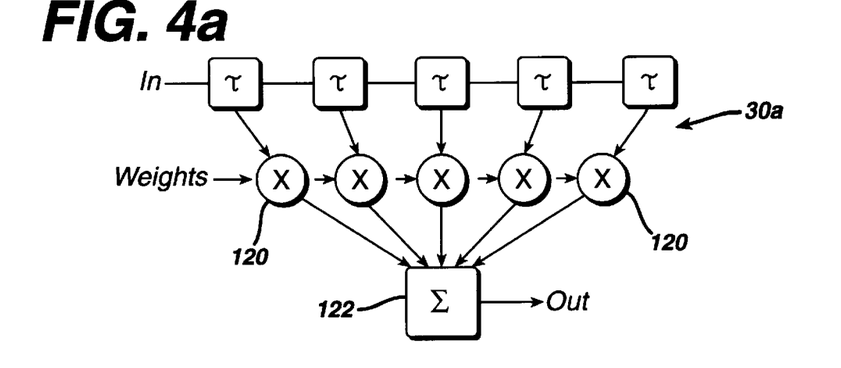
FIGS. 4a and 4b illustrate two alternate embodiments of the wall filter of FIG. 1.
Figure 4B:
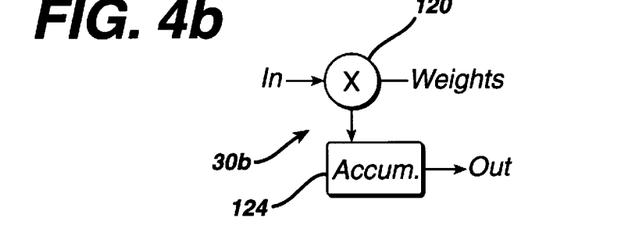

FIGS. 4a and 4b illustrate two other embodiments of the wall filter 30. The embodiment of FIG. 4a illustrates a finite impulse response (FIR) filter suitable for use as a wall filter. The echoes of the ensemble are shifted into the series of delay stages τ. As the ensemble passes through the delay stages the samples are multiplied by weighting factors in the multipliers 120 to give the signals the desired filtered characteristic, and the products summed in a summing stage 122 which produces a sequence of filtered output signals. FIG. 4b illustrates a filter formed by a multiplier 120 and an accumulator 124. In this embodiment the echoes of the ensemble are sequentially multiplied by weighting factors applied to the multiplier 120 and the products are accumulated in an accumulator 124. The multiplier-accumulator embodiment may be cascaded to produce higher rate output signals, since a series of multiply operations must be sequentially performed before a complete output value is accumulated in the accumulator. Outputs of either of these filter embodiments can be periodically skipped to give the resultant outputs a decimation filter characteristic. Because the ensemble is a finite length sequence, care must be given to initialization so that the filter does not "ring" as processing begins. This may be done by padding initialization values ahead of the echo values using DC values or replicating several of the initial values of the sequence. The finite filter length also means that the response of the filter will be affected by the length of the ensemble being filtered; longer sequences of samples will have a greater number of coefficients, weighting factors, and products, enabling the production of more complex and more sharply tailored filter characteristics.

Figure 5A:
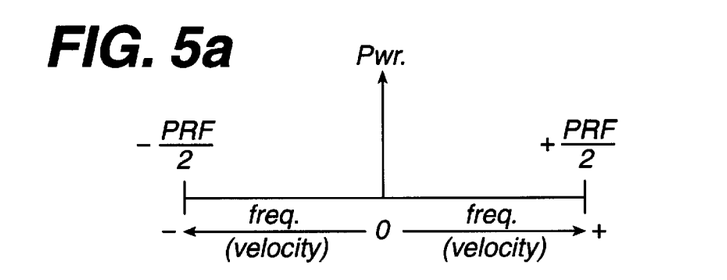
FIG. 5a illustrates a conventional Doppler spectrum and FIG. 5b illustrates a Doppler spectrum produced in accordance with the principles of the present invention.

The Doppler spectrum produced by conventional Doppler processing is shown in FIG. 5a. Since the Doppler response is effectively sampled by the transmitted pulses, the PRF sets the Nyquist limit for the range of Doppler frequencies which can be detected without aliasing. Because motion or flow can be either toward (+) or away from (−) the transducer, the limits of the spectrum are −(PRF/2) and +(PRF/2) and centered about a frequency reference of zero. The ordinate is a measure of Doppler power. Since the Doppler shift frequency corresponds directly to the velocity of motion the abscissa can be stated in both the Doppler frequency and velocity. Doppler signals returned from stationary objects will be located at the central zero velocity axis. The Doppler shift of signals from moving blood or tissue will be located to the left or right of the central axis, depending upon the direction of motion, with lower velocities closer to the central axis and greater velocities located toward the extremes of the abscissa.

Figure 5B:
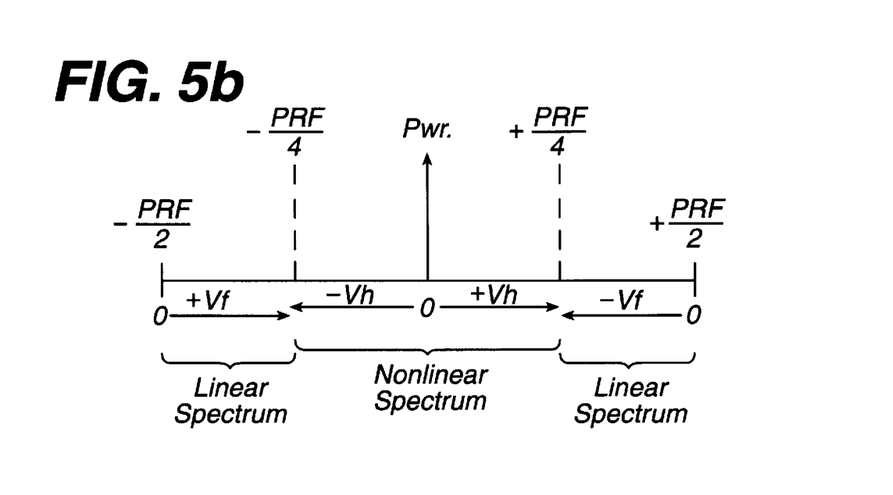
Figure 6A:
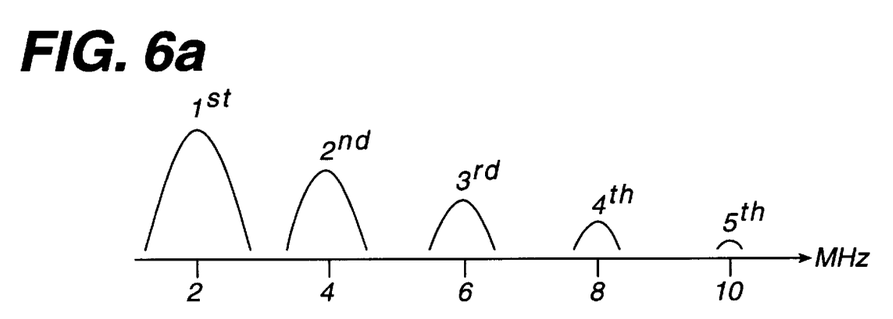
FIG. 6 illustrates the separation of different harmonic spectra in accordance with the principles of the present invention.
Figure 6B:
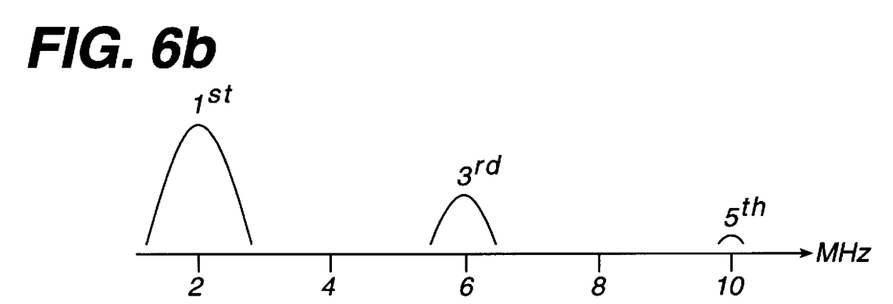
Figure 6C:
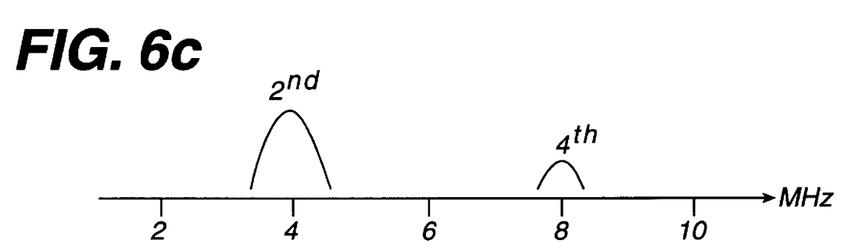
Figure 6D:
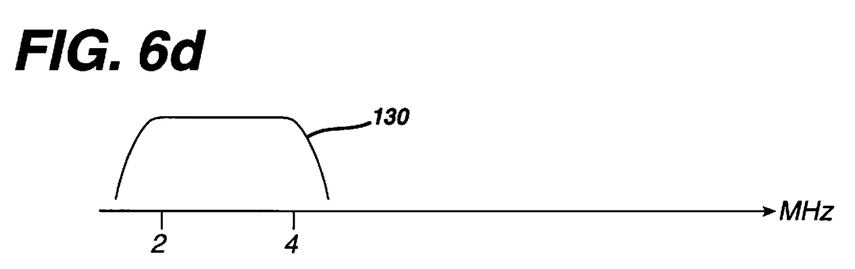

A Doppler spectrum resulting from practice of the present invention is shown in FIG. 5b. Like the conventional spectrum the Doppler spectrum of FIG. 5b is bounded by the Nyquist limits of −(PRF/2) and +(PRF/2) and is centered about a zero velocity ordinate. However, the phase alteration of the transmit signal from pulse to pulse effects a partition of the Doppler shift spectrum into odd (linear+higher order nonlinear) and even (second harmonic+higher order nonlinear) component regions, and a translation of stationary linear components, such as those returned from stationary tissue, to the extremes of the spectrum. The nonlinear region where second harmonic components reside is bounded by −(PRF/4) and +(PRF/4) and is centered about the central axis. Tissue harmonic components returned from stationary tissue will be found at the central axis, and harmonic components returned from moving substances such as flowing harmonic contrast agents will be found outward from the central axis toward the −(PRF/4) and +(PRF/4) boundaries, as indicated by the arrows marked $-V_h$ and $+V_h$. The region where linear components reside, such as fundamental frequency components returned from stationary and moving tissue and blood, is located outward from the −(PRF/4) and +(PRF/4) boundaries. Fundamental components from stationary materials will be located at the −(PRF/2) and +(PRF/2) extremes of the spectrum, with signal components from materials of increasing velocity located inward of the extremes as indicated by the arrows marked $+V_f$ and $-V_f$. Thus, by selecting signal components from the appropriate region, a user can image or perform analysis of the desired segmented signal component including linear signals from stationary targets, nonlinear signals from stationary targets, linear signals from moving targets, or nonlinear signals from moving targets.

A mathematical explanation of the practice and results of the present invention is as follows. A series of N ultrasonic wave pulses are transmitted at a pulse repetition interval of T seconds. Each transmitted pulse is an inverted copy of the previous pulse:

$$p_k(t) = (-1)^k p_0(t - kT), k \in [0, N-1] \quad (1)$$

where $p_k(t)$ is the pressure waveform of transmit pulse k. The received echoes, $e_k(t)$, are demodulated by mixing them in quadrature with a carrier at a frequency $f_c$, typically chosen either near the center of the transducer passband (for broadband transmit pulsing), or at or near the second harmonic of the transmit frequency (for narrowband transmit pulsing). The demodulated signals are then processed to produce a Doppler spectrum.

For linear scattering structures, successive echoes will be of the form:

$$e_{k+1}(t-(k-1)T) = -e_k(t-kT-\Delta\tau_d), \quad (2)$$

where $\Delta\tau_d = 2\Delta d/c_s$ is a time delay due to an axial motion, $\Delta d$, of the scattering structure relative to the transducer between pulses ($c_s$ is the speed of sound in the medium). The corresponding phase shift between successive echoes, measured relative to $f_c$ will be:

$$\Delta\phi = 2\pi f_c \Delta\tau_{d+\pi} \quad (3)$$

The additional $\pi$ term is a consequence of the negative sign in front of $e_k$ in equation 2. The estimated Doppler frequency will thus be:

$$f_d = \frac{\Delta\phi}{2\pi} f_{pr} = \frac{2v}{c_s} f_c + \frac{1}{2} f_{pr}, \quad (4)$$

where v is the relative axial velocity of the scatterer with respect to the transducer, and $f_{pr}=1/T$ is the pulse repetition frequency (PRF). Thus, the signals from linear scatterers will appear shifted in the Doppler spectrum by an amount equal to the Nyquist frequency.

Echoes from nonlinear scattering can be decomposed into odd and even components as follows:

$$\text{Echo}\{p(t)\} = e_{even}(t) + e_{odd}(t) \quad (5)$$

$$\text{Echo}\{-p(t)\} = e_{even}(t) - e_{odd}(t) \quad (6)$$

For successive PID echoes, the $e_{odd}(t)$ component changes sign with P(t), but the $e_{even}(t)$ component does not. This decomposition is general and does not rely on the exact nature of the scattering process. For the simple model of:

$$\text{Echo}\{p(t)\} = \sum_{k=0}^{\infty} a_k p^k(t-\tau) \quad (7)$$

$e_{odd}(t)$ will contain echoes due to the odd-ordered scattering terms and $e_{even}(t)$ will contain echoes due to the even-ordered scattering terms.

The Doppler shifts due to these two components are:

$$f_{d,odd} = \frac{2v}{c_s} f_c + \frac{1}{2} f_{pr} \quad (8)$$

$$f_{d,even} = \frac{2v}{c_s} f_c \quad (9)$$

Note that $f_{d,even}$ has a Doppler shift identical to that produced by conventional Doppler.

Providing all scatterer velocities obey a revised Nyquist limit:

$$\frac{2|v_{max}|}{c_s} f_c \leq \frac{1}{4} f_{pr}, \quad (10)$$

which is half of the conventional limit, the portion of the Doppler spectrum between $-f_{pr}/4$ and $f_{pr}/4$ will contain only Doppler signals arising from nonlinear scattering processes (this is referred to herein as the low frequency or nonlinear portion of the spectrum). The remaining half of the Doppler spectrum (referred to as the high frequency or linear portion) will contain Doppler signals arising from both linear scattering and possibly higher order nonlinear scattering.

The frequency separation produced by the phase alteration of the transmit waves in accordance with the present invention is complementary as shown in FIG. 6. FIG. 6a shows a band of fundamental frequencies about a nominal frequency of 2 MHz received in response to a nominal transmit frequency centered at 2 MHz, succeeded by second, third, fourth and fifth harmonic bands centered about 4, 6, 8 and 10 MHz, respectively. The spectral division performed by pulse inversion transmission and subtractive combination of the acquired signals is shown in FIG. 6b. The odd-ordered harmonics including the fundamental are separated by this processing. Correspondingly, pulse inversion transmission with additive combining will divide out the even-ordered harmonics, including the second harmonic, as shown in FIG.

6c. The spectra of FIG. 6b thus reside in the regions marked "linear" in FIG. 5b, and the spectra of FIG. 6c reside in the region marked "nonlinear" in FIG. 5b. However, it must be remembered that ultrasonic imaging transducers have finite passbands. The passband exhibited by the P4-2 phased array transducer produced by ATL Ultrasound, Inc. of Bothell, WA is approximately as shown by the passband 130 of FIG. 6d, which is substantially flat from 2 MHz to 4 MHz. The P4-2 phased array transducer will thus reproduce the fundamental and second harmonic bands shown above passband 130, and higher order bands will be eliminated by the upper cutoff of the transducer. The nonlinear and linear spectra imaged by the P4-2 transducer will therefore be composed of fundamental and second harmonic components, without significant energy of the higher order harmonics. This means that the P4-2 transducer can be used to image either solely the fundamental or second harmonic echoes of a 2 MHz transmitted wave.

FIGS. 7–10 illustrate examples of the spectra of different Doppler signals which may be acquired in a variety of diagnostic imaging procedures in accordance with the present invention. FIG. 7a illustrates the spectrum of echoes from substantially stationary tissue following low intensity wave transmission. Substantially all spectral components are linear and are located in bands 202,204 at the Nyquist extremes of the Doppler spectrum. When the intensity of the transmitted energy is increased, the spectrum of FIG. 7b results. The same stationary linear bands 202,204 are present. But the increased transmit energy causes a more rapid buildup of harmonic components in the transmitted wave and second harmonic energy is now contained in the echoes returned from stationary tissue as shown by the band 206 located about the central (stationary) axis of the nonlinear region of the spectrum.

Figure 7A:
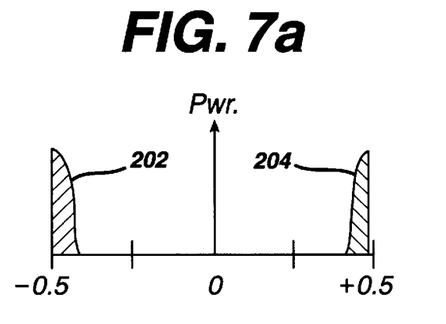
FIGS. 7–10 illustrate spectra of different types of ultrasonic information which may be analyzed or imaged in accordance with the principles of the present invention.
Figure 7B:
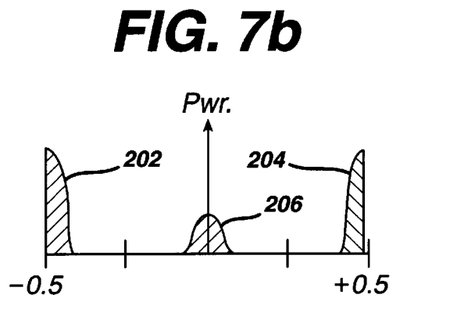
Figure 12:
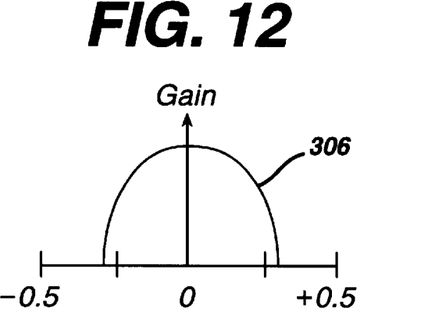

If one wanted to form an image of only the second harmonic tissue components in the spectrum of FIG. 7b, one could adjust the coefficients of the matrix filter or the weights of the FIR filter to give the filter a simple response characteristic such as that shown by filter passband 306 in FIG. 12. It can be seen that this filter passband will pass the tissue harmonic components in the center of the passband but not the fundamental components outside the passband 306. Thus, the wall filter is used to select the type of signal components to be used for further processing.

Figure 8A:
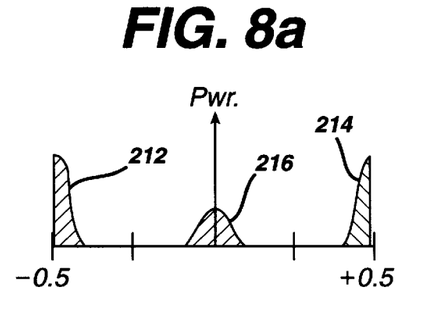
Figure 8B:
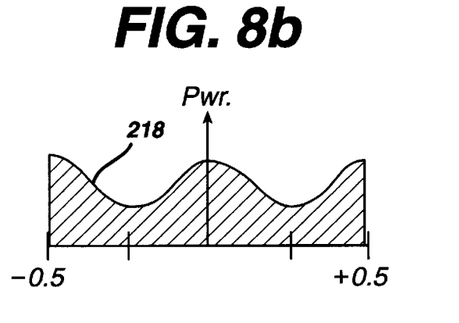

FIG. 8a illustrates the content of a spectrum which can result from detection of a harmonic contrast agent in perfused tissue such as the perfused myocardium at low transmit intensities. The contrast agent will reflect linear components of the transmitted wave as indicated by bands 212,214, and also nonlinear signal components due to the nonlinear characteristics of the agent as shown by the nonlinear band 216. All of these bands are located about the zero velocity center and extremes of the Doppler band, which is to be expected from the slow flow rate of contrast agent through the tissue. When the transmitted energy is increased to disrupt the contrast agent microbubbles, the spectrum of these events is broadened significantly, generally broadening to fill the entire Doppler spectrum as shown by band 218 in FIG. 8b. The signal components of band 218 can be effectively displayed in the power Doppler format, or differentiated and amplitude detected as described in U.S. Pat. No. 5,456,257.

Figure 9A:
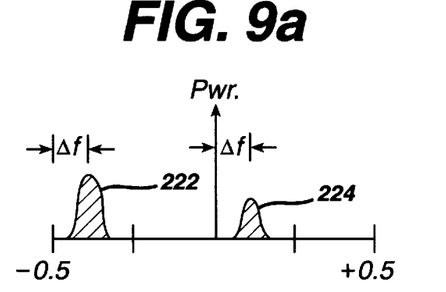
Figure 9B:
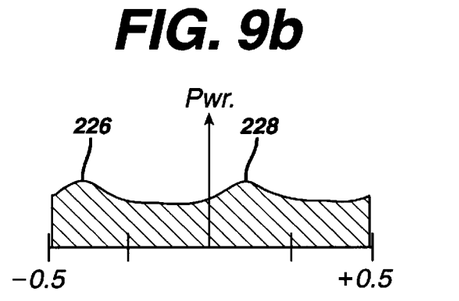

FIG. 9a illustrates the spectrum of a flowing contrast agent in a blood vessel. As expected, both the fundamental and harmonic bands of the contrast agent echo have moved away from the stationary axes by a frequency (velocity) $\Delta f$ as indicated by the positions of bands 222,224, where $\Delta f = 2vf_c/c$ (see equation (9)). When the flowing contrast agent is exposed to higher transmit energy, the disruption of the microbubbles will return a spectrum as shown in FIG. 9b. This spectrum is broad due to the broadband energy released by the disruption of the microbubbles, and is also peaked at the frequencies 226,228 corresponding to the fundamental and second harmonic returns of the flowing agent at its velocity of travel.

Figure 10A:
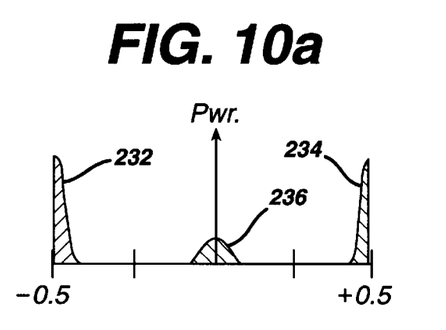
Figure 10B:
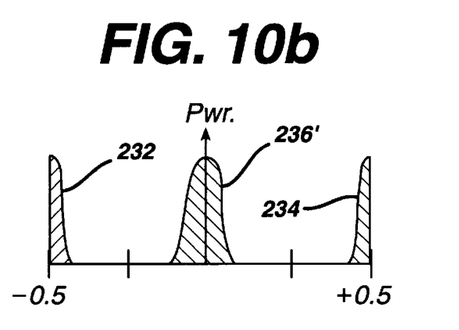

FIG. 10a illustrates the spectrum of energy returned by stationary tissue in the absence of any contrast agent in response to moderate transmit energy. The echoes return fundamental frequency energy as shown by bands 232,243, and a moderate amount of tissue harmonic energy in band 236. When the transmitted energy is substantially increased, the harmonic energy of the transmitted waves builds up at a greater rate, as indicated by the greater amplitude of band 236' in FIG. 10b.

The spectra and bands of FIGS. 7–10 assume that the sampling rate (PRF) of the transmit waves satisfies the Nyquist criterion for the velocities of flow or motion encountered. If high velocities are undersampled, the harmonics of the resultant spectrum will only be partially separated in regions where the sampling rate criterion is satisfied; higher velocities which are undersampled will overlap to the other harmonic region of the spectrum.

Figure 11A:
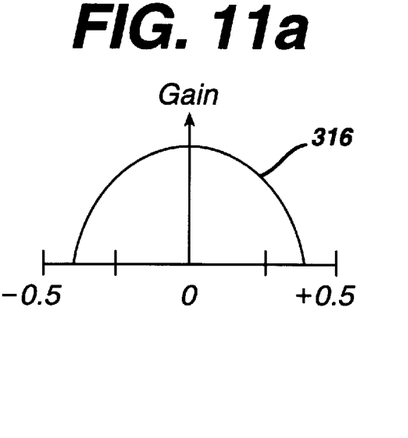
FIGS. 11–15 illustrate wall filter characteristics for delineating the different types of ultrasonic information of the spectra of FIGS. 7–10.
Figure 11B:
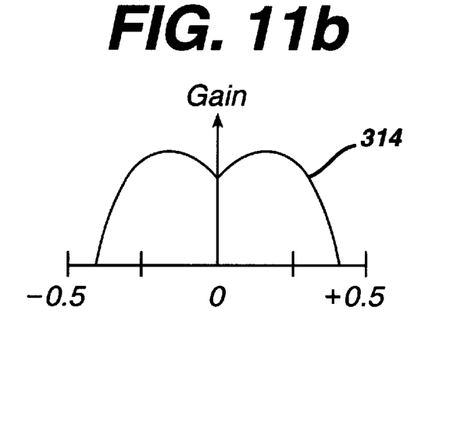
Figure 11C:
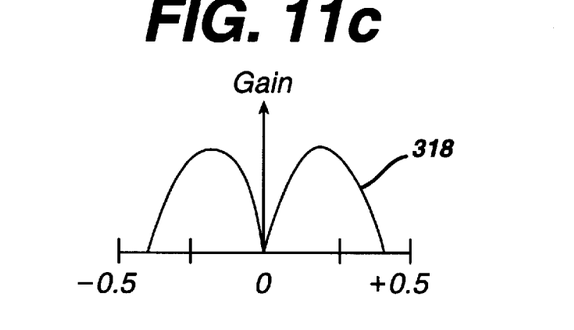

FIGS. 11–15 illustrate a number of passbands which can be developed by the choice of coefficients and weights for the wall filter. The spectral drawings of FIGS. 11–15, like FIGS. 7–10, show unlabeled PRF/4 demarcations on the abscissa. More complex functions generally require higher order filters and greater ensemble lengths. FIG. 11 illustrates wall filter passbands useful for detecting harmonic contrast agents in the myocardium, the spectra of FIG. 8. At low transmit energy the passband 316 of FIG. 11a can be used to maximize the low velocity gain at the center of the nonlinear region so as to maximize returns from band 216 of FIG. 8a. At more moderate energy the passband 314 of FIG. 11b could be used to give greater gain in the low velocity nonlinear region as microbubble disruption begins. At high energy the passband 318 of FIG. 11c could be used to reject linear components (at the spectral extremes) and harmonic components from stationary tissue (at the center of the spectrum), while maximizing the broadband return from the disruption of the contrast agent microbubbles. In short, the filter gains in the different regions of the Doppler spectrum can be used to reduce or increase the signal gain in one region of the spectrum relative to another region.

Figure 13:
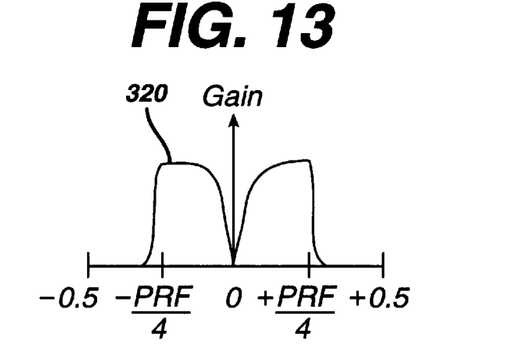

FIG. 13 illustrates a carefully tailored passband 320 for colorflow imaging of harmonic contrast agents in accordance with the present invention. Components from tissue harmonics are rejected at the center of the spectrum, and the full passband gain is applied over the full harmonic frequency (velocity) range out to the PRF/4 boundaries.

Figure 14:
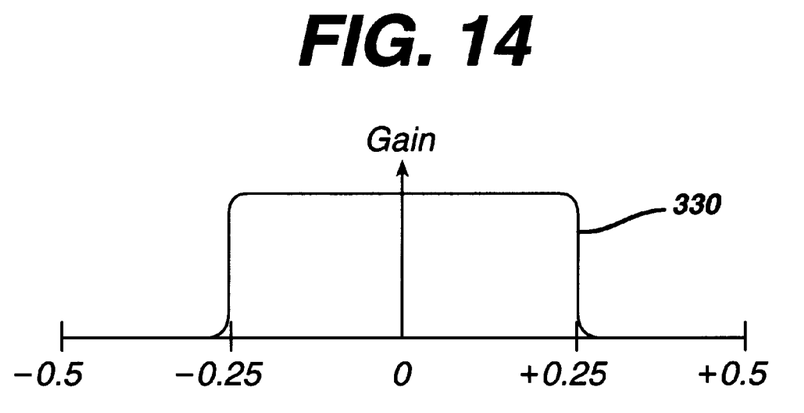
Figure 15:
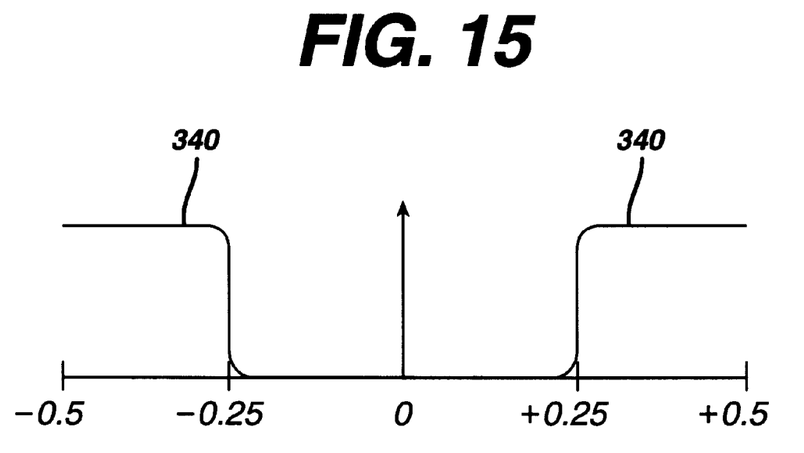

FIGS. 14 and 15 illustrate idealized passbands for second harmonic (and other even-ordered nonlinear) and fundamental (and odd-ordered nonlinear) signals. Passband 330, with its sharp cutoff at PRF/4, will pass second harmonic nonlinear signals from all sources, harmonic contrast agents and tissue harmonics. The complementary passband 340 of FIG. 15 will pass linear (fundamental) signal components from all sources.

It is also envisioned that some procedures may call for multiple filters to separate two regions of the spectrum for one image or analytical procedure. For example, two filters could be used to separately pass the odd harmonic (linear) and even harmonic bands of FIG. 9, respectively, and separately Doppler process each set of signals. This would enable the display of a flowing contrast agent from the even harmonic information within the moving walls of the beating heart, by tissue Doppler processing of the fundamental signal information. As a second example, one filter could be used to derive the nonlinear signal intensity (using a response characteristic as shown in FIG. 14) and the other filter used to derive the linear signal intensity (using a response characteristic as shown in FIG. 15), both of which may be processed by power Doppler processing. The ratio of the nonlinear signal power to the linear signal power at each pixel location in an image plane could then be computed and displayed. In a preferred embodiment this nonliner to linear ratio is computed by squaring the linear value in the denominator to make the resulting parameter less power dependent. Matrix wall filters lend themselves well to such "two channel" implementation, since an expanded coeffficient set can produce products for two passbands which are separately accumulated and then Doppler processed. The coefficients used to process the linear region of the Doppler spectrum can have polarities which invert every other echo in the ensemble during the multiplication process to remodulate the linear components distributed about ±(PRF)/2 down to zero in the odd-ordered channel.

The present inventors have found that power Doppler is the preferred Doppler technique for most applications and produces excellent images in most instances where the presence but not the direction of flow is required. Power Doppler images of myocardial perfusion have been produced with excellent resolution of the perfused cardiac tissue. Color Doppler imaging in accordance with the present invention is highly useful for imaging renal transplants, for instance. Grayscale presentations are also possible. While Doppler ensembles can generally range from lengths of two to sixteen samples, it has been found that excellent results can be achieved with shorter ensemble lengths; power Doppler images with two sample ensembles have been found to produce highly resolved images and also afford a high realtime frame rate. Longer transmit pulses may be desirable in certain circumstances. The present inventors have also found that two samples obtained from moving tissue by the pulse inversion technique can be effectively imaged by the power motion imaging technique using the power motion processor 50 in FIG. 1. Details of the power motion imaging technique and processor 50 can be found in U.S. Pat. No. 5,718,229.

Other modulation techniques for introducing an echo-to-echo variance in the received ensemble may be used with acceptable effect. For instance, the amplitudes of successive transmitted pulses can be alternated between two different levels, with or without a 180° phase shift from pulse to pulse, and the received echoes normalized according to transmit pulse amplitude, then processed as described above. The amplitude modulation will effect a variation sufficient to cause some separation of linear and nonlinear components sufficient to carry out the techniques of the present invention. If the 180° phase shift is not used, then the odd-ordered portion of the spectrum and the even-ordered portion will be reversed. While this is considered to be a sub-optimal implementation of the present invention, it may be effective or desirable in certain circumstances.

The principles of the present invention are readily applicable to PW Doppler applications where the Doppler spectrum is displayed graphically or numerically. Thus, by choice of the desired wall filter the Doppler spectrum of linear or nonlinear signal components can be selectively processed and displayed.

Since pulse inversion Doppler clearly separates nonlinear scattering from linear scattering, it is well suited to the detection of microbubble contrast agents in linear tissue. Furthermore, this technique allows broadband, high resolution pulses to be used in Doppler applications.

What is claimed is:

1. A method for ultrasonically analyzing linear or nonlinear ultrasonic echo signal components comprising the steps of:

transmitting a sequence of phase-varying ultrasonic waves into the body;

receiving a sequence of ultrasonic echo signals in response to said phase-varying ultrasonic waves;

analyzing the phase shifts between successive echoes to separate the phase shifts of odd and even harmonic signal components; and utilizing at least one of said separate odd and even harmonic signal components.

2. The method of claim 1, wherein said step of transmitting comprises transmitting a sequence of ultrasonic waves which vary in phase by 180° from one wave to the next.

3. The method of claim 1, wherein said step of analyzing comprises Doppler processing said sequence of ultrasonic echo signals.

4. The method of claim 3, wherein said step of Doppler processing includes filtering Doppler shift signals with a predetermined filter characteristic.

5. The method of claim 1, wherein said step of utilizing comprises producing an ultrasonic image using said separated harmonic signal components.

6. The method of claim 1, wherein said step of utilizing comprises displaying a quantified Doppler measurement using said separated harmonic signal components.

7. The method of claim 1, wherein said step of receiving comprises receiving a sequence of temporally distinct echoes from a given target location.

8. The ultrasonic diagnostic imaging system of claim 1, wherein said sequence of ultrasonic echo signals comprises a sequence of three or more echo signals.

9. A method for mapping r.f. ultrasonic echo signal information to the Doppler domain in a manner which separates linear and nonlinear signal information comprising the steps of:

transmitting a sequence of phase-varying ultrasonic waves into the body;

receiving an ensemble of ultrasonic echo signals in response to said phase-varying ultrasonic waves; and Doppler processing said ensemble of echo signals to produce Doppler phase shift information separated in accordance with the linearity of the echo signals.

10. The method of claim 9 wherein said step of transmitting comprises transmitting a sequence of ultrasonic waves which vary in phase by 180° from one wave to the next.

11. The method of claim 10, wherein said step of Doppler processing includes filtering Doppler shift signals with a predetermined filter characteristic.

12. The method of claim 11, wherein said step of filtering comprises wall filtering said ultrasonic echo signals.

13. The method of claim 9, wherein said step of receiving comprises receiving an ensemble of temporally distinct echoes from a given target location.

14. The method of claim 9, wherein said step of Doppler processing comprises Doppler processing an ensemble of echo signals from tissue.

15. The method of claim 9, wherein said step of Doppler processing comprises Doppler processing an ensemble of echo signals from moving tissue.

16. The method of claim 9, wherein said step of Doppler processing comprises Doppler processing an ensemble of echo signals from tissue which contain second harmonic signal components.

17. The method of claim 9, wherein said step of Doppler processing comprises Doppler processing said ensemble of echo signals to produce velocity information.

18. The method of claim 9, wherein said step of Doppler processing comprises Doppler processing said ensemble of echo signals to produce power Doppler information.

19. A method for differentiating linear and nonlinear ultrasonic echo signal components comprising the steps of:
   transmitting a modulated sequence of three or more ultrasonic waves into the body to generate phase distinctions in resulting ultrasonic echoes;
   receiving an ensemble of three or more ultrasonic echo signals in response to said transmitted sequence; and
   analyzing said ensemble of echo signals to separate phase shift information of linear and nonlinear echo signal components in the presence of motion.

20. The method of claim 19, wherein said step of transmitting comprises transmitting ultrasonic waves which are modulated from pulse to pulse.

21. The method of claim 20, wherein said transmit pulse modulation introduces a phase separation between linear and nonlinear signal components.

22. The method of claim 20, wherein said modulation occurs at the Nyquist limit of the rate of said transmit pulses.

23. The method of claim 20, wherein said modulation comprises a 180° phase variation from pulse to pulse, an amplitude modulation from pulse to pulse, or a combination of phase and amplitude modulation from pulse to pulse.

24. The method of claim 19, wherein said step of analyzing comprises differentially detecting linear and nonlinear signal components.

25. The method of claim 24, wherein said step of differentially detecting comprises power Doppler processing said ensemble.

26. The method of claim 24, wherein said step of differentially detecting comprises colorflow processing said ensemble.

27. A method for differentially phase modulating linear and nonlinear ultrasonic echo signal components comprising the steps of:
   transmitting a modulated sequence of ultrasonic waves into the body to generate phase distinctions in resulting ultrasonic echoes;
   receiving an ensemble of ultrasonic echo signals in response to said transmitted sequence; and
   analyzing said ensemble to separate phase shift information of linear and nonlinear signal components,
   wherein said step of transmitting comprises transmitting ultrasonic waves which are modulated from pulse to pulse,
   wherein said modulation comprises a 180° phase variation from pulse to pulse, an amplitude modulation from pulse to pulse, or a combination of phase and amplitude modulation from pulse to pulse, and
   wherein said step of analyzing comprises Doppler processing said ensemble of echo signals to produce Doppler phase shift information separated in accordance with the linearity of the echo signals.

28. The method of claim 27, wherein said step of Doppler processing includes filtering Doppler shift signals with a predetermined filter characteristic.

29. The method of claim 28, wherein said step of filtering comprises wall filtering said ultrasonic echo signals.

30. A method of separating linear and nonlinear ultrasonic signal components comprising the steps of:
   transmitting a sequence of ultrasonic waves into the body which are differently amplitude or phase modulated from one wave to another;
   receiving an ensemble of ultrasonic echo signals in response to said modulated ultrasonic waves, each of which contains both linear and nonlinear echo signal components; and
   processing said received ensemble of echoes to produce separated nonlinear phase shift components in the presence of motion.

31. The method of claim 30, wherein said step of processing comprises Doppler processing an ensemble of echo signals from moving tissue.

32. The method of claim 30, wherein said step of processing comprises Doppler processing an ensemble of echo signals from tissue which contain second harmonic signal components.

33. The method of claim 30, wherein said step of processing comprises Doppler processing said ensemble of echo signals to produce velocity information.

34. The method of claim 30, wherein said step of processing comprises Doppler processing said ensemble of echo signals to produce power Doppler information.

35. The method of claim 30, wherein said step of processing produces a spectrum comprising separate frequency bands of odd harmonic component frequencies and even harmonic component frequencies.

36. The method of claim 30, wherein said step of receiving comprises receiving an ensemble of three or more ultrasonic echo signals.

37. An ultrasonic diagnostic imaging system which separates odd and even harmonic ultrasonic echo information comprising:
   an ultrasonic wave transmitter which transmits a sequence of phase-varying ultrasonic waves into a subject;
   an ultrasonic wave receiver which receives a sequence of ultrasonic echo signals in response to said phase-varying ultrasonic waves; and
   a phase shift processor which processes said sequence of echo signals on the basis of relative phase characteristics to separate received echo information into odd and even harmonic signal components.

38. The ultrasonic diagnostic imaging system of claim 37, wherein said transmitter transmits a sequence of ultrasonic waves which vary in phase by 180° from one wave to the next.

39. The ultrasonic diagnostic imaging system of claim 37, wherein said phase shift processor comprises a Doppler processor.

40. The ultrasonic diagnostic imaging system of claim 39, wherein said Doppler processor includes a Doppler shift filter.

41. The ultrasonic diagnostic imaging system of claim 37, further comprising an image processor for producing an ultrasonic image using said separated harmonic signal components.

42. The ultrasonic diagnostic imaging system of claim 37, further comprising an image processor which displays a quantified Doppler measurement using said separated harmonic signal components.

43. The ultrasonic diagnostic imaging system of claim 37, wherein said receiver receives a sequence of temporally distinct echoes from a given target location.

44. The ultrasonic diagnostic imaging system of claim 37, wherein said sequence of ultrasonic echo signals comprises a sequence of three or more echo signals.

45. An ultrasonic diagnostic imaging system which separates linear and nonlinear ultrasonic signal information comprising:

an ultrasonic wave transmitter which transmits a sequence of phase-varying ultrasonic waves into a subject;

a receiver which receives an ensemble of ultrasonic echo signals in response to said phase-varying ultrasonic waves; and a Doppler processor which processes said ensemble of echo signals to produce Doppler phase shift information delineated in accordance with the linearity of said ultrasonic echo signals.

46. The ultrasonic diagnostic imaging system of claim 45, wherein said Doppler processor includes a Doppler shift filter.

47. The ultrasonic diagnostic imaging system of claim 46, wherein said filter comprises a wall filter.

48. The ultrasonic diagnostic imaging system of claim 45, wherein said Doppler processor processes an ensemble of echo signals from tissue.

49. The ultrasonic diagnostic imaging system of claim 45, wherein said Doppler processor processes an ensemble of echo signals from moving tissue.

50. The ultrasonic diagnostic imaging system of claim 45, wherein said Doppler processor processes an ensemble of echo signals from tissue which contain second harmonic signal components.

51. The ultrasonic diagnostic imaging system of claim 45, wherein said Doppler processor processes said ensemble of echo signals to produce velocity information.

52. The ultrasonic diagnostic imaging system of claim 45, wherein said Doppler processor processes said ensemble of echo signals to produce power Doppler information.

53. An ultrasonic diagnostic imaging system which distinguishes linear and nonlinear ultrasonic echo signal components comprising:

an ultrasonic wave transmitter which transmits a modulated sequence of ultrasonic waves into a subject;

a receiver which receives an ensemble of ultrasonic echo signals in response to said modulated transmit sequence of ultrasonic waves; and a processor responsive to said ensemble which separates linear echo signal components including those resulting from motion and nonlinear echo signal components.

54. The ultrasonic diagnostic imaging system of claim 53, wherein said transmitter transmits ultrasonic waves which are modulated from pulse to pulse.

55. The ultrasonic diagnostic imaging system of claim 54, wherein said transmit pulse modulation introduces a phase separation between linear and nonlinear signal components.

56. The ultrasonic diagnostic imaging system of claim 54, wherein said modulation occurs at the Nyquist limit of the rate of said transmit pulses.

57. The ultrasonic diagnostic imaging system of claim 54, wherein said modulation comprises a 180° phase variation from pulse to pulse, an amplitude modulation from pulse to pulse, or a combination of phase and amplitude modulation from pulse to pulse.

58. The ultrasonic diagnostic imaging system of claim 53, wherein said processor comprises a differential processor which differentially detects linear and nonlinear signal components.

59. The ultrasonic diagnostic imaging system of claim 53, wherein said ensemble of ultrasonic echo signals comprises an ensemble of three or more echo signals.

60. An ultrasonic diagnostic imaging system which distinguishes linear and nonlinear ultrasonic echo signal components comprising:

an ultrasonic wave transmitter which transmits a modulated sequence of ultrasonic waves into a subject;

a receiver which receives an ensemble of ultrasonic echo signals in response to said modulated transmit sequence of ultrasonic waves; and a processor which separates phase shift information of said echoes into linear and nonlinear signal components, wherein said processor comprises a differential processor which differentially detects linear and nonlinear signal components, and wherein said processor comprises a power Doppler processor.

61. An ultrasonic diagnostic imaging system which distinguishes linear and nonlinear ultrasonic echo signal components comprising:

an ultrasonic wave transmitter which transmits a modulated sequence of ultrasonic waves into a subject;

a receiver which receives an ensemble of ultrasonic echo signals in response to said modulated transmit sequence of ultrasonic waves; and a processor which separates phase shift information of said echoes into linear and nonlinear signal components, wherein said processor comprises a differential processor which differentially detects linear and nonlinear signal components, and wherein said processor comprises a colorflow processor.

62. An ultrasonic diagnostic imaging system which distinguishes the harmonic signal effects of moving tissue comprising:

a transmitter which transmits a sequence of phase-varying ultrasonic waves into a subject;

a receiver which receives an ensemble of echoes in response to said ultrasonic waves; and a tissue Doppler processor which processes said ensemble to distinguish a spectrum of the odd or even harmonic signal effects of moving tissue.

63. The ultrasonic diagnostic imaging system of claim 62, wherein said transmitted waves introduce a phase shift of 180° into Doppler signal information.

64. The ultrasonic diagnostic imaging system of claim 63, wherein said introduced phase shift translates odd harmonic signal components to a different region of said Doppler spectrum than that occupied by even harmonic signal components.

65. The ultrasonic diagnostic imaging system of claim 62, wherein said ensemble of echoes comprises an ensemble of three or more echo signals.

66. An ultrasonic diagnostic imaging system which distinguishes the harmonic signal effects of moving tissue or harmonic contrast agents comprising:

a transmitter which transmits a sequence of phase-varying ultrasonic waves into a subject;

a receiver which receives an ensemble of echoes in response to said ultrasonic waves; and a power Doppler processor which processes said ensemble to distinguish a spectrum of the odd or even harmonic signal effects of moving tissue or of a harmonic contrast agent.

67. The ultrasonic diagnostic imaging system of claim 66, wherein said transmitter transmits a sequence of ultrasonic waves which vary in phase from one wave to the next.

68. The ultrasonic diagnostic imaging system of claim 66, wherein said transmitted waves introduce a phase shift of 180° into Doppler signal information.

69. The ultrasonic diagnostic imaging system of claim 68, wherein said introduced phase shift translates odd harmonic signal components to a different region of said Doppler spectrum than that occupied by even harmonic signal components.

70. The ultrasonic diagnostic imaging system of claim 69, wherein each of said regions includes a range of frequencies corresponding to velocities of even or odd harmonic reflectors, including zero velocities.

71. An ultrasonic diagnostic imaging system which separates odd and even harmonic ultrasonic signal information comprising:

an ultrasonic wave transmitter which transmits a sequence of phase-varying ultrasonic waves into a subject;

a receiver which receives an ensemble of ultrasonic echo signals in response to said phase-varying ultrasonic waves; and a Doppler processor which processes said ensemble of echo signals to produce Doppler phase shift information; and first and second filters which pass odd harmonic Doppler phase shift information and even harmonic Doppler phase shift information, respectively.

72. The ultrasonic diagnostic imaging system of claim 71, further comprising a ratio circuit coupled to said first and second filters for computing a ratio of odd and even harmonic phase shift information.

73. The ultrasonic diagnostic imaging system of claim 72, wherein said ratio comprises the ratio of nonlinear signal information to linear signal information.

74. The ultrasonic diagnostic imaging system of claim 71, further comprising an image processor coupled to said first and second filters for producing an image containing odd and even harmonic phase shift information.

75. The ultrasonic diagnostic imaging system of claim 71, wherein said filters comprise wall filters.

76. The ultrasonic diagnostic imaging system of claim 75, wherein said filters comprise a maxtrix filter which produces two matrix results.

* * * * *